United States Patent
Guirguis et al.

(10) Patent No.: US 6,277,646 B1
(45) Date of Patent: Aug. 21, 2001

(54) FLUID SPECIMEN COLLECTING AND TESTING APPARATUS

(75) Inventors: Raouf A. Guirguis, Vienna, VA (US); Dean Haldopoulos, Smyrna, GA (US); Michael R. Pratt, Chevy Chase, MD (US); Brian K. Harmison, Herndon, VA (US)

(73) Assignee: Dade Behring Inc., Deerfield, IL (US)

( * ) Notice: Subject to any disclaimer, the term of this patent is extended or adjusted under 35 U.S.C. 154(b) by 0 days.

(21) Appl. No.: 08/971,695

(22) Filed: Nov. 17, 1997

Related U.S. Application Data

(63) Continuation-in-part of application No. 08/851,548, filed on May 5, 1997, now abandoned.

(51) Int. Cl.[7] .................................................. G01N 33/48
(52) U.S. Cl. ........................... 436/165; 436/174; 422/58; 422/61; 422/102
(58) Field of Search ................................. 422/102, 99, 61, 422/68.1, 58; 436/164–166, 170, 174, 177

(56) References Cited

U.S. PATENT DOCUMENTS

| | | |
|---|---|---|
| 3,894,845 | 7/1975 | McDonald . |
| 4,473,530 | 9/1984 | Villa-Real . |
| 4,736,859 | 4/1988 | Mayes et al. . |
| 4,812,293 * | 3/1989 | McLaurin et al. ..................... 422/69 |
| 4,927,605 * | 5/1990 | Dorn et al. ............................ 422/102 |
| 4,979,402 * | 12/1990 | Ryan et al. ............................ 73/863 |
| 5,119,830 * | 6/1992 | Davis .................................... 128/771 |
| 5,312,593 * | 5/1994 | Rabenecker et al. ................. 422/86 |
| 5,393,496 * | 2/1995 | Seymour ............................... 422/101 |
| 5,425,921 * | 6/1995 | Coakley et al. ...................... 422/102 |
| 5,429,803 * | 7/1995 | Guirguis ................................. 422/58 |
| 5,624,554 * | 4/1997 | Faulkner et al. ..................... 210/232 |
| 5,652,143 * | 7/1997 | Gombrich et al. ................. 435/304.2 |
| 5,658,531 * | 8/1997 | Cope et al. ............................. 422/58 |
| 5,849,505 * | 12/1998 | Guirguis ................................ 435/7.2 |
| 5,854,076 * | 12/1998 | Kundu et al. .......................... 436/69 |
| 5,869,003 * | 2/1999 | Nason .................................... 422/58 |

FOREIGN PATENT DOCUMENTS

| | | |
|---|---|---|
| 0332572 | 9/1989 | (EP) . |
| 9404929 | 3/1994 | (WO) . |
| 9507659 | 3/1995 | (WO) . |

\* cited by examiner

*Primary Examiner*—Lyle A. Alexander
(74) *Attorney, Agent, or Firm*—Leland K Jordan; Lois K Ruszala

(57) ABSTRACT

A device is provided for both collecting and testing a fluid specimen. The device includes a specimen container having a collection chamber, an isolation chamber and a test chamber. The collection chamber is in fluid communication with the isolation chamber and sealed from the test chamber. The isolation chamber is also sealed from the test chamber. The fluid specimen is collected in the collection chamber and an aliquot is isolated in the isolation chamber. A fluid releasing element is provided to release fluid from the isolation chamber and establish a flow path to the test chamber while sealing the isolation chamber from the collection chamber. In accordance with another aspect of the present invention, the specimen container may include a tamper evident lid which provides an identification of whether or not the container has been opened which may indicate that the contents of the container have been compromised.

24 Claims, 11 Drawing Sheets

FLUID SPECIMEN COLLECTING AND TESTING APPARATUS

RELATED APPLICATIONS

This application is a continuation-in-part of patent application Ser. No. 08/851,548, filed May 5, 1997 now abandoned.

FIELD OF THE INVENTION

The present invention is directed to a fluid specimen collecting and testing apparatus suitable for field or laboratory use. More particularly, the present invention is directed to an apparatus for collecting and testing biological fluids in a single apparatus while preserving the integrity of the originally collected specimen.

BACKGROUND OF THE INVENTION

In the health-care industry, diagnostic testing of body fluids is a common place activity. Employers, government agencies, sports teams and other organizations have also become increasingly involved in diagnostic testing to maintain safety in the workplace and to ensure compliance with laws, rules and regulations.

It is generally necessary in diagnosing and testing for the presence of a predetermined analyte (e.g. drugs and/or disease) to collect biological fluids from an animal or human, i.e., urine, blood, sputum, pleural, cavity and peritoneal cavity fluids for analysis. Maintaining the integrity of the collected biological fluid specimens is vital to obtaining reliable test results and to preserving an uncontaminated sample for subsequent confirmatory testing. It is of utmost importance during the collection and handling of biological fluid specimens that the potential for specimen contamination be minimized or eliminated. It is also important to minimize the potential for specimen damage during the collection process and testing process.

Many known devices for collecting and testing body fluids involve multiple steps and/or multiple containers. Generally, these devices require collection of a fluid specimen in one device, isolation or segregation of the fluid specimen into an aliquot in the same device and transfer of the specimen to a different device for analysis. Separate collection, and testing requires an undesirable amount of handling of the specimen and is likely to lead to unacceptable levels of contamination.

There is a long felt need in the industry for a unitary device that performs collection, isolation and testing of a specimen that preserves the integrity of a portion of the specimen, isolates a separate portion of the specimen for testing, and minimizes the risk of misidentification. One of the difficulties in realizing such a device is that current federal regulations prohibit mixing the collected specimen with the aliquot specimen or the test specimen. Existing prior art devices that perform collection, isolation and testing have not adequately maintained separation between the collected fluid specimen, the aliquot and the test specimen. These devices have also failed to provide a totally sealed system in that bodily fluids leak to the outside environment. Furthermore, existing prior art devices have experienced undesirably high error rates in their function and in their test results.

SUMMARY OF THE INVENTION

The present invention involves an integrated fluid collection and testing apparatus that may be used with any type of fluid specimen, and is particularly useful for urine, blood and saliva specimens. The apparatus collects a fluid specimen, isolates a predetermined portion of the specimen, and exposes only the isolated portion of the specimen to diagnostic or testing structures and/or reagents. The isolated portion may be isolated as the fluid is collected in the apparatus, i.e., without any additional manipulation by testing personnel. The isolated portion is then independently tested in isolation from the collected fluid specimen.

In accordance with one embodiment of the invention, the fluid specimen collecting and testing apparatus includes a collecting chamber for collecting the fluid specimen, an isolation chamber for isolating an aliquot of the fluid specimen for testing, and a test chamber or region for testing the specimen. In accordance with the invention, the collection chamber is never in fluid communication with or open to the test chamber. Preferably, when the collection chamber is in fluid communication with the isolation chamber, the test chamber is closed to the isolation chamber. When the isolation chamber is in fluid communication with the test chamber, the collection chamber is closed to the isolation chamber. Preferably, the isolation chamber is in fluid communication with the collection chamber so that the aliquot can be readily isolated without complex manipulation by collection personnel. A test chamber is provided for performing diagnostic testing on the aliquot.

Furthermore, in accordance with the invention, the isolated portion of the fluid does not contact the remainder of the collected sample once the isolated portion comes in contact with contaminating structures or reagents. In accordance with the invention, the collected sample is maintained in a pristine or unadulterated state. Such a characteristic of the present invention is advantageous in that it permits independent and/or confirmatory testing of the same sample that was screened using a device of the present invention. Also in accordance with the invention, a totally closed (sealed) system is provided which prevents the fluid specimen from leaking to the outside environments. Other advantages will be clear to those skilled in the art upon reading the description and drawings below.

In view of the importance of testing the aliquot in isolation from the collected fluid specimen, the test chamber is sealed from the collection chamber. To initiate testing, communication between the isolation chamber and the test chamber is established. In a preferred embodiment of the invention, a fluid releasing device is provided that opens the communication between the isolation chamber and the test chamber and establishes a fluid flow path to the test chamber. To prevent undesirable flow through the collected fluid specimen to the test chamber via the isolation chamber, the fluid releasing device may also establish a seal between the collecting chamber and the isolation chamber.

In accordance with another aspect of the present invention, the specimen container may include a tamper evident lid which provides an identification of whether or not the container has been opened which may indicate that the contents of the container have been compromised. In a preferred embodiment, a tamper strip may be releasably attached to the tamper evident lid which, in combination with the specimen container, permits one way rotation of the lid. Removal of the lid after closure to the locked position preferably results in partial or complete disconnection of the tamper strip from the lid. This feature reduces the possibility of sample adulteration and aids in ensuring the integrity of the diagnostic testing.

DETAILED DESCRIPTION OF THE INVENTION

Figure 1:
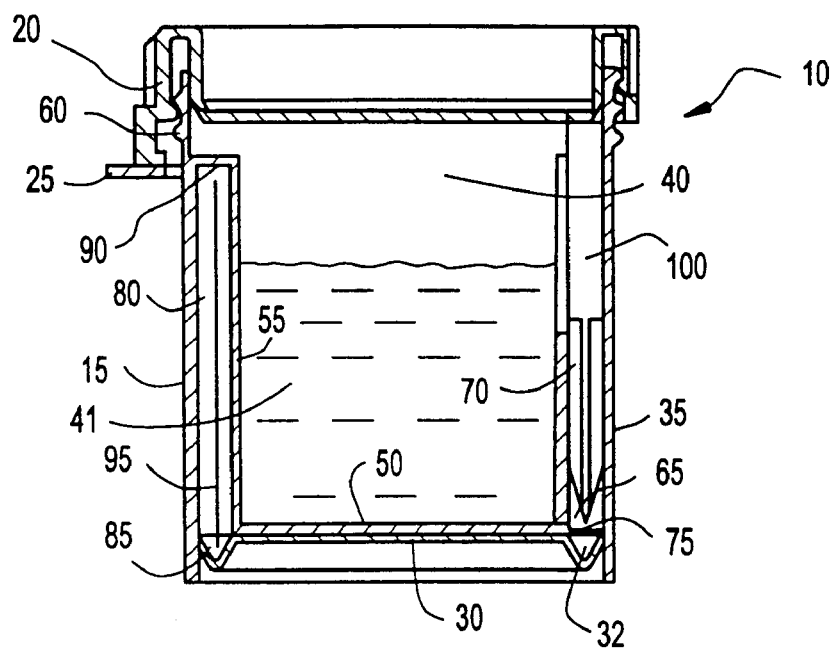
FIG. 1 depicts a cross sectional view of the fluid collecting and testing apparatus according to the present invention in a first phase of operation.

The present invention provides a unitary fluid collecting and testing apparatus for collecting fluid, isolating a portion of the fluid and performing diagnostic testing on the isolated fluid. The invention is particularly effective in collecting and testing human or animal body fluids such as blood, saliva or urine. The fluid may be untreated, e.g., taken directly from the subject, or may be mixed with a diluent, test reagent, preservative, anti-coagulant, or the like. In a preferred embodiment of the invention, if the fluid is combined with another substance, such action should occur only in the isolation chamber or test chamber.

The present invention also provides a method for treating a sample, or a method for collecting and testing a sample, that comprises collecting a sample to be tested, isolating a portion of the sample, and testing the isolated portion, wherein the isolating step and the subsequent testing step is completely separate from the remaining sample collected in the first step.

To ensure integrity in diagnostic testing, the collected fluid is completely isolated from the portion of the fluid exposed to the test reagents and/or structures. In one embodiment, the invention includes a specimen container provided with several chambers or regions. The specimen container may include a collection chamber for collecting the fluid specimen to be tested. The specimen container may also include an isolation chamber in fluid communication with the collection chamber for isolating an appropriate amount of fluid to be tested. In a preferred embodiment of the invention, the isolation chamber is sized to accommodate a pre-selected or pre-determined amount of fluid. However, the invention includes an isolation chamber of any size or configuration.

The specimen container may further include a test chamber for testing the fluid from the isolation chamber. The isolation chamber may be sealed or separated from the test chamber to preserve the integrity of the diagnostic test to be performed. Isolation refers to structure that separates the collection chamber from the testing chamber so that a fluid portion isolated for testing never recontacts the originally collected sample.

One skilled in the art will recognize that any of a number of tests can be used in conjunction with the present invention. Exemplary tests include, but are not limited to drugs, drugs of abuse, therapeutic drugs, PSA, insulin, cancer, cancer markers, infectious diseases, HIV, cholesterol, proteins, antigens, antibodies, allergens, and the like. Other exemplary tests are listed in U.S. Pat. No. 4,366,241, incorporated herein by reference. It is intended that the invention is not to be limited by the type or number of tests in each device. Exemplary tests and test methodologies are described in more detail below.

In order to initiate testing, a fluid releasing element is provided that activates or controls the movement of fluid from the collection chamber into the isolation chamber. In one embodiment of the invention, the apparatus comprises a fluid releasing element that breaks or opens a seal between the isolation chamber and the test chamber. The fluid releasing element also releases fluid from the isolation chamber into the test chamber and, concurrently seals the isolation chamber from the collecting chamber so that fluid is not able to flow from the collecting chamber directly into the test chamber.

Figure 3:
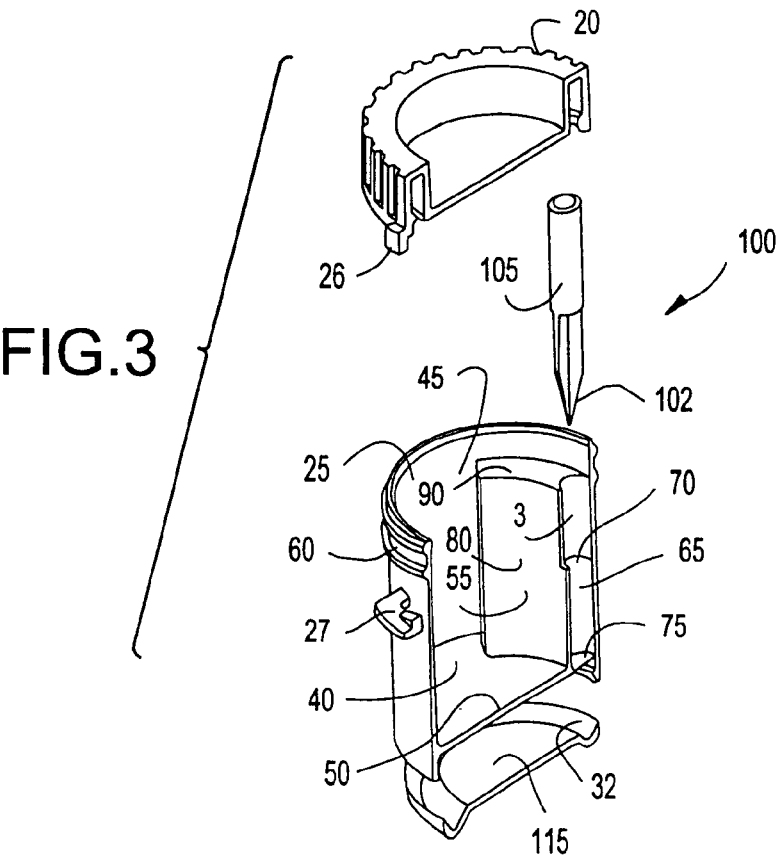
FIG. 3 is an exploded cut away view of the fluid specimen collecting apparatus according to the first embodiment of the present invention.

FIG. 1 illustrates a fluid specimen collection and testing apparatus 10, in accordance with the present invention. The apparatus generally includes a specimen container 15, and a cover or lid 20. The specimen container 15 has an opening 25, best shown in FIG. 3, that allows a fluid specimen to be placed into the container. Preferably, the specimen container 15 includes a bottom wall 50 and a generally cylindrical wall (container wall) 35 extending from the bottom wall 50, as shown in FIG. 3. A collection chamber 40 for collecting the fluid specimen, illustrated by element 41, may be disposed within or may be defined by the walls of the specimen container 15. The collection chamber 40 may preferably include an opening 45, a bottom wall 50 and a generally cylindrical wall (collection chamber wall) 55 extending from at least a portion of the bottom wall 50. The container wall 35 preferably includes a rim 60 that extends beyond the collection chamber wall 55. The rim 60 may be threaded to accommodate a screw-on lid 20. Alternatively, the rim 60 may include a flange or lip to accommodate a snap fit lid.

Figure 2:
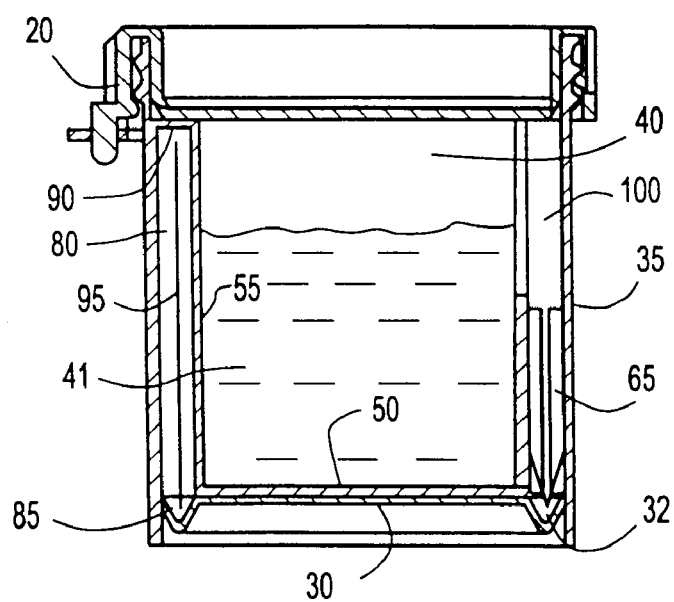
FIG. 2 illustrates a cross sectional view of the fluid collecting and testing apparatus according to the first embodiment of the present invention in a second phase of operation.
Figure 6:
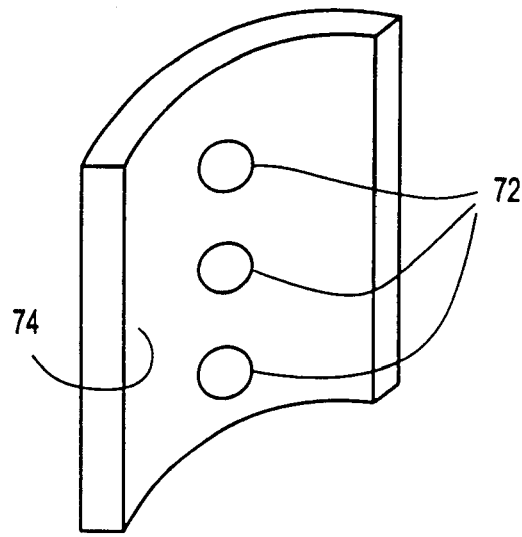
FIG. 6 illustrates a section of an isolation chamber in accordance with an alternative embodiment of the present invention.

Referring to FIGS. 1–3, an isolation chamber 65 is provided to isolate a predetermined portion, e.g., an aliquot, of the fluid specimen for testing. The isolation chamber 65 is arranged to be in fluid communication with the collection chamber 40. Preferably, the isolation chamber 65 may be disposed between the container wall 35 and the collection chamber wall 55 and extends from the bottom wall 50 of the collection chamber 40 to a point below the rim 60. The isolation chamber 65 may include an open end 70. In accordance with the present invention, the isolation chamber may include any of a number and/or quantity of structures that permit fluid to flow from the collection chamber into the isolation chamber. For example, the isolation chamber may include an open top end, as illustrated in FIGS. 1–3, or may include one or more apertures 72 or channels into an isolation chamber wall 74 of the isolation chamber, as illustrated in FIG. 6. Preferably, the open end 70 is positioned below the rim 60 to promote or permit fluid communication between the collection chamber 40 and the isolation chamber 65 so that as the collection chamber 40 is filled, the fluid specimen can freely flow to the isolation chamber 65. As the fluid enters isolation chamber 65, the air in isolation chamber 65 preferably may be displaced around the fluid releasing element 100 and through the collection chamber. The fluid releasing element 100 in an open position is not air tight which allows air to flow through the collection chamber and through opening 45.

The isolation chamber 65 may also include a frangible bottom wall 75, preferably a liquophobic seal such as a puncturable membrane. In a preferred embodiment, the frangible bottom wall 75 may be a thin layer of an olefinic, polymeric material, such as polypropylene or nylon. In a most preferred embodiment, the fluid contacting structures are liquophobic or hydrophobic, or may include a surface treatment that makes the surface liquophobic or hydrophobic. Such surface treatments, such as those used to change the critical surface tension (CST) or the critical wetting surface tension (CWST), are well known in the art. The frangible bottom wall may be raised from the bottom wall 50 of the specimen container 15.

In accordance with the invention, the specimen container 15 may be provided with one or more test regions or chambers 80. The test chamber 80 is sealed from the collection chamber 40 and is preferably sealed from the isolation chamber 65. The test chamber 80 may include an opening 85 that is preferably disposed proximate to the bottom wall 50 of the specimen container 15 and a closed end 90 that is preferably disposed proximate to the opening 25 of the specimen container 15. To facilitate diagnostic testing, the test chamber 80 may be provided with a test agent 95 of the type generally known in the art, i.e., a substance, device, or strip that reacts with one or more substances in the fluid specimen. Preferred test agents include test strips, e.g., antigen/antibody test strips such as any conventional immunochromatograph strip tests, as noted above.

Figure 4:
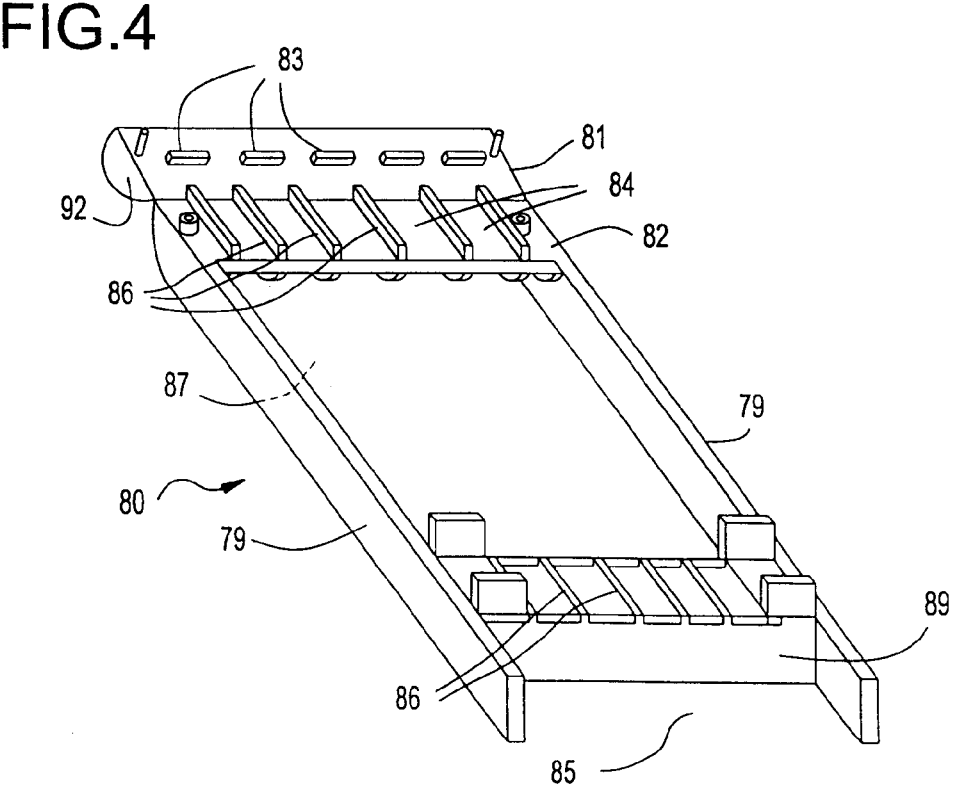
FIG. 4 illustrates a test chamber in accordance with one embodiment of the present invention.

In accordance with another embodiment of the invention, the test chamber 80 may be provided with a plurality of regions or chambers each of which contains a test agent 95 physically separated from the other test agents, as illustrated in FIG. 4. In this embodiment, test chamber 80 includes a top wall portion 92, side wall portions 79 and a back wall portion 87. The side walls 79 extend to the bottom wall 50 of the collection chamber 40, as illustrated in FIGS. 1 and 2. The bottom region of the test chamber 80 and the test agents 95 are in fluid communication with the fluid flow path 32 through opening 85. However, all of testing chamber 80 is physically isolated from and has a fluid tight seal that separates it from the collection chamber 40.

In this embodiment of the invention, the testing chamber may include one or more structures that position or place test agents 95 in a pre-determined location or place. For example, the top wall portion 92 of testing chamber 80 may contain structure for supporting and physically separating the test agents 95. In a preferred embodiment, test agent support elements 81 and 82 may be connected together by a hinge structure which enables relative rotation of the elements about the axis of the hinge, as illustrated in FIG. 4. When test agent support elements 81 and 82 are closed, protuberances 83 press against the test agents 95 thereby maintaining the test agents in the chambers or regions 84. Support elements 81 and 82 are closed to support test agent 95 prior to insertion or formation into the specimen container.

The test chamber may include spacers 86 to maintain multiple test agents 95 in a spaced apart relationship. Test chamber 80 may also include a flood wall 89 that prevents the fluid sample from contacting the test agents 95 at locations above the flood wall 89 other than through capillary action of the fluid specimen. Although five chambers or regions 84 are illustrated in FIG. 4, it is understood that a larger or smaller number of chambers may be provided. The test chamber 80 also may be curved to conform to a cylindrical shape of the wall 35 of the specimen container, as illustrated in FIG. 3.

The test chamber 80 illustrated in FIG. 4 represents only one embodiment for positioning or supporting test agents 95 in a predetermined locations and is not intended to be limiting. Other structures may also be used as would be known by those skilled in the art. In one embodiment, test chamber 80 is integral to the specimen container and the collection chamber (i.e., it is formed at least partially of walls of those structures). In another embodiment, test chamber 80 may be a cassette which may be inserted into the region between a wall of the collection chamber and a wall of the specimen cup.

The apparatuses and methods of the present invention may be used to perform a number of tests and/or a number of test methodologies. In one embodiment of the invention, a method or apparatus according to the invention includes test structures for performing one or more tests for a single analyte. For example, such a device or method may include at least one test strip for detecting a drug of abuse. In another embodiment, a method or apparatus according to the invention includes test structures for performing multiple tests for multiple analytes. For example, such a device or method may include at least two test strips, preferably about five or six test strips, with each test strip testing for a different analyte. For example, such a device or method may test for the presence of THC, cocaine or its metabolites, PCP, a barbiturate, and an opiate. The device or method also may test for, e.g., amphetamines or benzothiazapines.

In accordance with the invention, to promote or permit fluid communication between the isolation chamber 65 and the test chamber 80, a fluid releasing element 100 is provided that opens the isolation chamber 65 and releases fluid from the isolation chamber 65 allowing the fluid to be directed to the test chamber 80. In addition, the fluid releasing element 100 seals the isolation chamber 65 from the collecting chamber concurrently with releasing the fluid from the isolation chamber 65 (as illustrated in FIG. 2). As described above, the isolation chamber 65 may include a frangible bottom wall 75. In accordance with a preferred embodiment, the fluid releasing element 100 penetrates or breaks the frangible bottom wall 75. Thus, fluid releasing element 100 may include a penetrating portion at one end which preferably is in the form of a spike 102. Other suitable penetrating members include a plunger, a plug, or any like device. For example, see plug 140 described below in connection with FIGS. 9–11.

Alternatively, the fluid releasing element may be any structure the movement of which permits fluid to flow into the isolation chamber or the test chamber. As described in more detail below, the fluid releasing element may be any shape, and is preferably shaped to conform to the channel or shape of the isolation chamber. For example, in an open, unactivated, or first position, illustratively shown in FIG. 1, the fluid releasing element permits fluid to flow in and around its base or lower end. In its closed, activated, or second position, illustratively shown in FIG. 2, the fluid releasing element opens communication between the fluid and the test chamber. At the same time, the shape of a portion 105 of the fluid releasing element 100, in conjunction with the one or more portions of the isolation chamber, seals the isolation chamber from the collection chamber.

Advantageously, the fluid releasing element 100 not only penetrates the frangible bottom wall 75 of the isolation chamber 65 but also seals the isolation chamber 65 from the collection chamber 40. To facilitate sealing, the fluid releasing element 100 may include a top portion 105 which forms a fluid tight seal in the open end 70 of isolation chamber 65, as illustrated in FIG. 2, thereby preventing fluid communication between the collection chamber 40 and the isolation and testing chambers. Sealing may be initiated by applying pressure to the fluid releasing element 100 to force the top portion 105 thereof into engagement with the side walls of the isolation chamber 65 thus creating a fluid tight seal. For example, as the lid 20 is coupled to the container, the lid 20 may contact a top portion of the fluid releasing element 100 and drive the device through the frangible bottom wall 75 of the isolation chamber 65 while plugging the open end 70 of the isolation chamber 65, as illustrated in FIG. 2.

Figure 5:
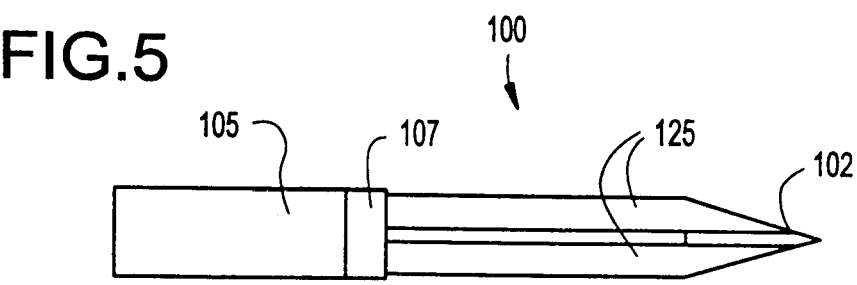
FIG. 5 is a side view of the fluid releasing device according to one embodiment of the present invention.

Fluid releasing element 100 preferably includes the top portion 105 at one end and the spike 102 at the opposite end. The top end 105 preferably may be of a size and shape to complement the size and shape of the isolation chamber 65 and, as pressure is applied, to form a fluid tight seal therewith. The fluid releasing element 100 and the isolation chamber 65 are preferably cylindrically shaped, but other shapes, e.g., square or rectangular, also may be used. Alternatively, the fluid releasing element 100 may have a diameter or thickness that gradually tapers from one end of the device to the other. For example, FIG. 5 illustrates a top portion 105 and spike 102 which are gradually tapered in the direction of spike 102. In such an embodiment, as pressure is applied to the fluid releasing element 100, a top portion of fluid releasing element 100 forms a friction fit, fluid tight seal over the open end 70 of the isolation chamber 65.

In another embodiment, fluid releasing element 100 includes a fluid tight seal section 107, as illustrated in FIG. 5. Fluid tight seal section 107 has a uniform diameter and is sized to form a fluid tight seal with open end 70 of isolation chamber 65 as the fluid releasing device is driven through the frangible bottom wall 75.

In operation, fluid is moved from one portion of the apparatus to another portion of the apparatus in phases or steps that prevent the isolated portion of the collected sample from re-contacting the remainder of the collected sample. In a first phase, the apparatus functions as a fluid specimen collection device. FIG. 1, depicts the apparatus in the first phase. Fluid may be readily placed in the device through the container opening and collected in the collection chamber 40. As the collection chamber 40 is filled, a portion of the fluid specimen may be transferred to the isolation chamber 65 because the isolation chamber 65 and the collection chamber 40 are in fluid communication. In a second phase, the fluid specimen collected in the isolation chamber 65 is passed to the test chamber 80 for diagnostic testing. FIG. 2 depicts the apparatus in the second phase. This stage may be initiated by coupling the lid 20 to the specimen container 15 to activate the fluid releasing element 100. When the lid 20 is coupled with specimen container 15, the fluid releasing element 100 is driven through the frangible bottom wall 75 to direct the fluid specimen to the fluid flow path 32 and to the test chamber 80. In addition, the fluid releasing element 100 arrests fluid flow from the collection chamber 40 to the isolation chamber 65 in such a manner as to prevent establishment of a direct flow path between the collection chamber 40 and the test chamber 80.

Alternatively, a first stage may include collecting the fluid in the collection chamber 40, a second stage may include transferring the portion of the fluid from the isolation chamber 65, and a third stage may include transferring the portion of the fluid from the isolation chamber 65 into test chamber 80.

In an embodiment of the invention, it may be desirable to isolate or separate a predetermined portion or amount of fluid from the collected fluid. As used herein, a predetermined portion refers to the quantity of fluid that is collected in the isolation chamber, or the amount of fluid that is exposed to the test structures. As may be recognized by one skilled in the art, it may be desirable to select the amount of fluid isolated in the isolation chamber by adjusting the size and/or shape of the spike relative to the size and/or shape of the isolation chamber. In a preferred embodiment of the invention, the predetermined amount is approximately equal to the void volume in the isolation chamber when the fluid releasing element is in its first or inactivated position. In a most preferred embodiment of the invention, a predetermined amount is an aliquot, or about 1.5 cc.

For example, as illustrated in FIGS. 3 and 5, spike 102 preferably includes grooves 125 which are sized to permit, in combination with the diameter of the isolation chamber 65, a predetermined amount of fluid in the isolation chamber 65. The predetermined amount is most preferably an aliquot of fluid, typically about 1.5 cc. The isolation chamber 65 and grooves 125, of course, may be sized to permit fluid amounts greater or lesser than about 1.5 cc.

In these embodiments, fluid communication between collection chamber 40 and isolation chamber 65 may be accomplished by any means that is closeable. As used herein, closeable refers to engagement of one or more portions or structures to establish a fluid tight seal that separates the fluid in the collection chamber from the fluid in the isolation chamber or the fluid in the test chamber. In accordance with the invention, various alternative structures may be involved, either separately or in combination. For example, in one embodiment of the invention a top portion of the fluid releasing element may engage the side walls of the isolation chamber to form a fluid tight fit and/or closing open end 70. Alternatively, if the isolation chamber 65 is closed at the top and includes one or more spaced apertures 72 in an isolation chamber wall 74, as illustrated in FIG. 6, spike tip 105 may engage wall 74 to form a fluid tight fit and/or closing of apertures 72.

To facilitate fluid communication between the isolation chamber 65 and the test chamber 80, the specimen container 15 may include a fluid flow path 32. The open end 85 of the test chamber 80 communicates with the fluid flow path 32. When the frangible bottom wall 75 of the isolation chamber 65 is opened as described above, the isolation chamber 65 is coupled to the fluid flow path 32 and the fluid specimen is free to flow along the fluid flow path 32 to the test chamber 80, while the fluid in the collection chamber 40 is inhibited from flowing into the isolation chamber 65 and the test chamber 80.

Fluid flow path 32 is formed by any structure or structures that establish fluid communication between the isolation chamber and the test chamber. In one embodiment of the invention, the fluid flow path is the space below the frangible wall 75. In this embodiment of the invention, test agents 95 are positioned directly below or adjacent to frangible wall 75. In a preferred embodiment of the invention, the fluid flow path 32 includes additional structures that further separate the test region from the frangible wall 75. An exemplary configuration is shown in the Figures.

Figure 9:
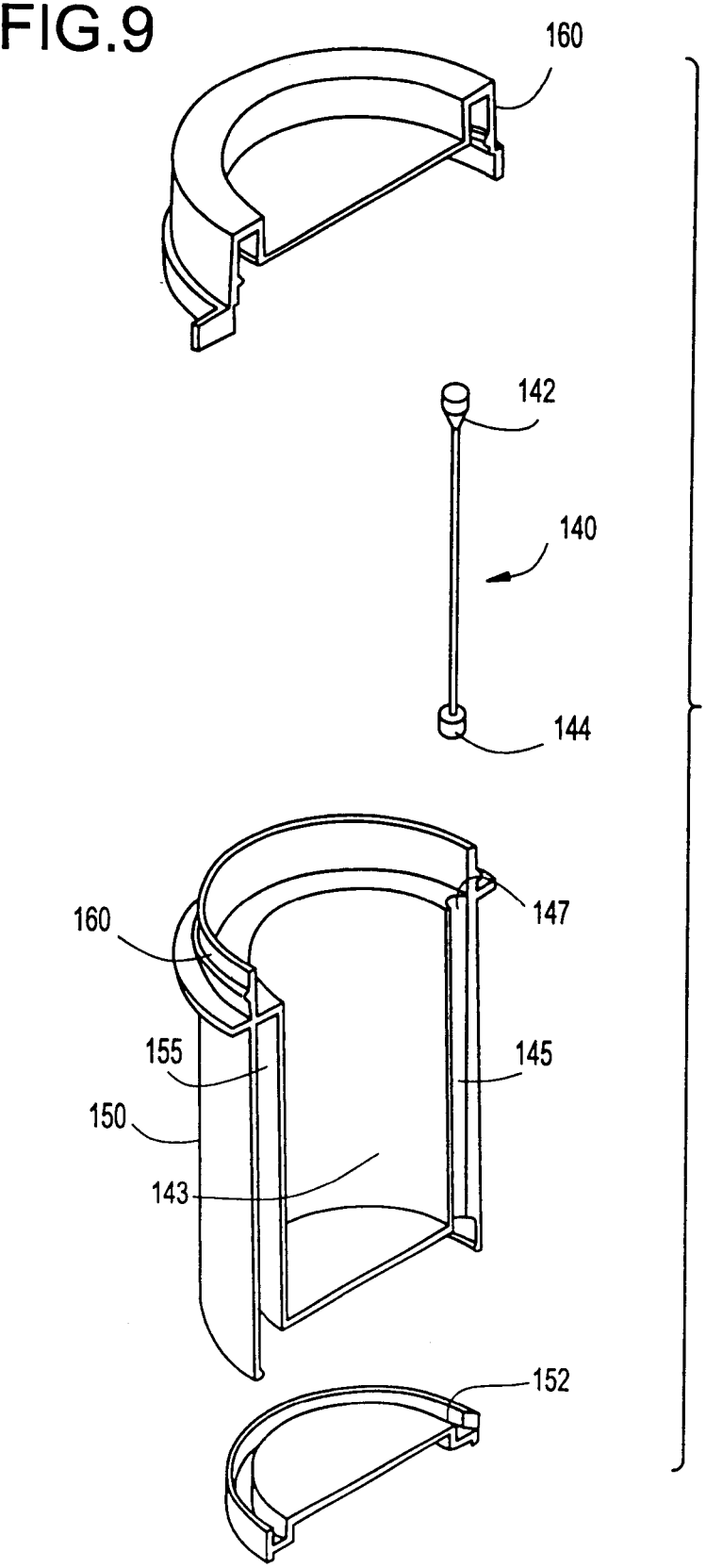
FIG. 9 is an exploded cut away view of the fluid specimen collecting apparatus according to an alternative embodiment of the present invention.
Figure 10:
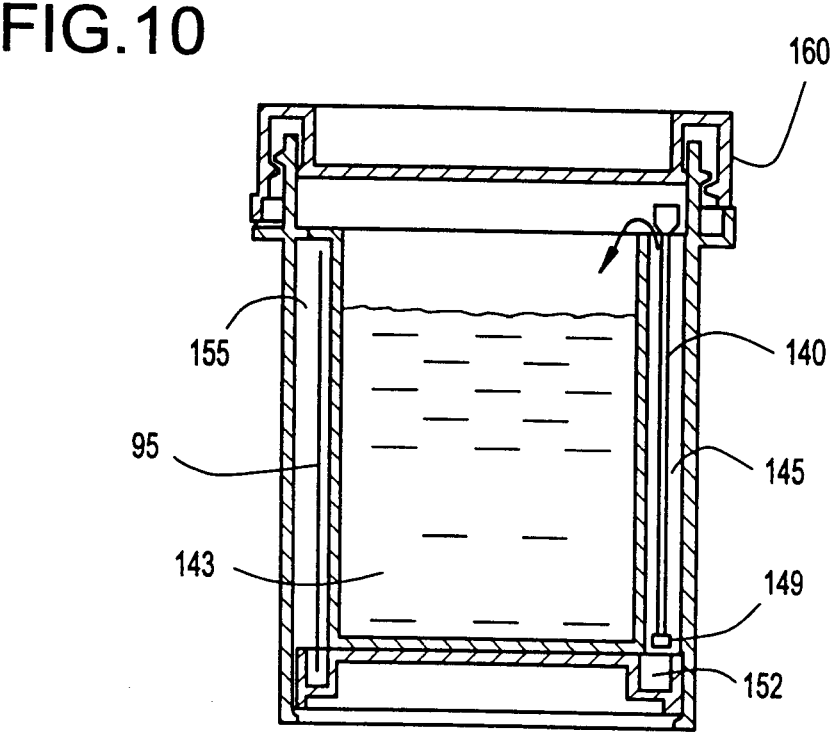
FIG. 10 depicts a cross sectional view of the fluid collecting and testing apparatus according to an alternative embodiment of the present invention in a first phase of operation.
Figure 11:
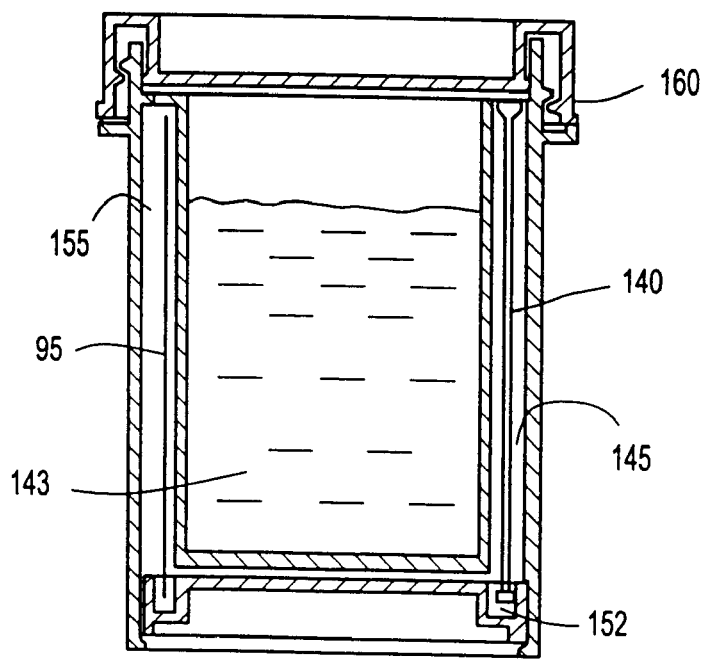
FIG. 11 illustrates a cross sectional view of the fluid collecting and testing apparatus according to the alternative embodiment of the present invention in a second phase of operation.

In a preferred embodiment, the fluid flow path 32 forms a groove-shaped channel having a generally "V-shaped" cross section, as illustrated in FIGS. 1–3. While not intending to be limited by a particular theory of operation, it is believed that the groove-shaped flow path 32 causes the fluid sample to be concentrated toward the bottom of the groove-shaped structures thereby facilitating maximum utilization of the fluid sample. In another embodiment, the fluid flow path may be provided with structures known to those skilled in the art which restrict fluid flow to only a portion of the entire flow path, such as for example, the portion between the isolation chamber and the testing chamber. Such fluid flow restriction also may facilitate maximum utilation of the fluid sample. The fluid flow path 32 may have other shapes as illustrated in FIGS. 9–11.

In one embodiment, the fluid flow path 32 may be formed from a bottom wall 30. The bottom wall 30 may be integrally formed with the specimen container 15 or may be a structural insert that is sealed to the bottom of the specimen container 15. In accordance with an embodiment of the invention, the bottom wall 30 may include a platform 115 which contacts the lower wall of the collection chamber 40. The fluid flow path 32 may traverse the platform 115, or, as shown in the Figures, may circumscribe the platform 115. In another embodiment, the fluid flow path 32, without bottom wall 30, is integrally formed with the specimen container 15. Although not necessary for the operation of the invention, and in yet another embodiment, a wick may be provided in the fluid flow path between the isolation chamber and the test chamber.

Figure 7:
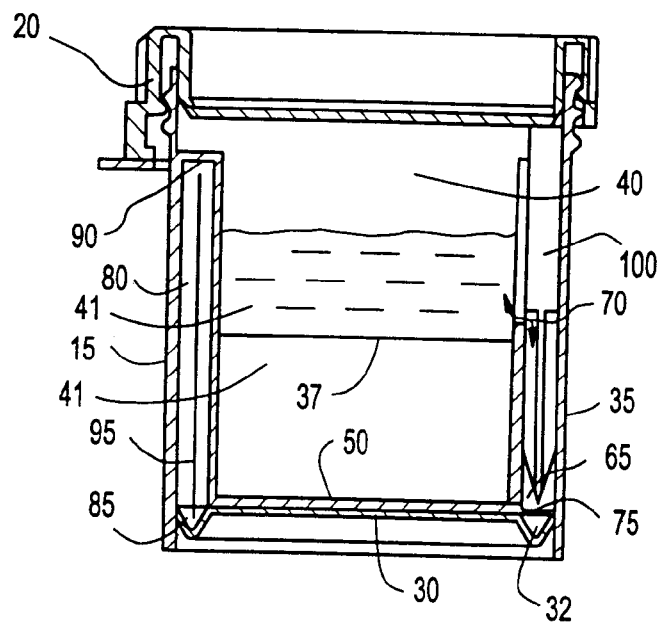
FIG. 7 illustrates a cross sectional view of the specimen collecting cup in accordance with another alternative embodiment of the present invention.

The present invention may be used to collect and test fluid samples having varying sizes. For example, a urine or blood sample from a child may be smaller than such a sample from an adult. Saliva samples also tend to be smaller in volume. In an alternative embodiment, the specimen container 15 may include a false bottom wall 37 in collection chamber 40, as illustrated in FIG. 7, which reduces the volume of sample needed to create fluid communication between collection chamber 40 and the isolation chamber 65. Preferably, false bottom wall 37 may be placed at any location between the bottom wall 50 and the open end 70 of isolation chamber 65 to accommodate a fluid sample of any size. In another embodiment, false bottom wall 37 may have an angled or sloped portion which angles or slopes down to the open end 70 of isolation chamber 65. For example, in this embodiment, the false bottom wall may be conically shaped (not shown) which drains into open end 70 of the isolation chamber.

It should be noted that the lid 20 may be provided with a stop so that the lid 20 may be engaged with the specimen container 15 without activating the fluid releasing device 100. For example, in one embodiment, the lid 20 may be provided with a tab 26 and the specimen container may be provided with a tab lock 27, as illustrated in FIG. 3. In this embodiment, lid 20 is rotatable around the rim 60 of the specimen container 15 until tab 26 engages the tab lock 27 thereby preventing any further rotation of the lid 20, as illustrated in FIG. 1. At this stage of rotation, the lid 20 preferably forms a fluid tight seal with the specimen container 15 and fluid releasing element 100 does not penetrate the frangible bottom wall 75. To activate the fluid releasing element 100, the tab lock preferably is pushed down or broken off to release and permit further rotation of the lid 20. The lid 20 then may be further rotated around rim 60, driving the fluid releasing element 100 down, and rupturing the frangible bottom wall 75, as illustrated in FIG. 2. In an alternative embodiment, the tab 26, and not the tab lock 27, may be removed permitting further rotation of the lid 20.

Figure 8:
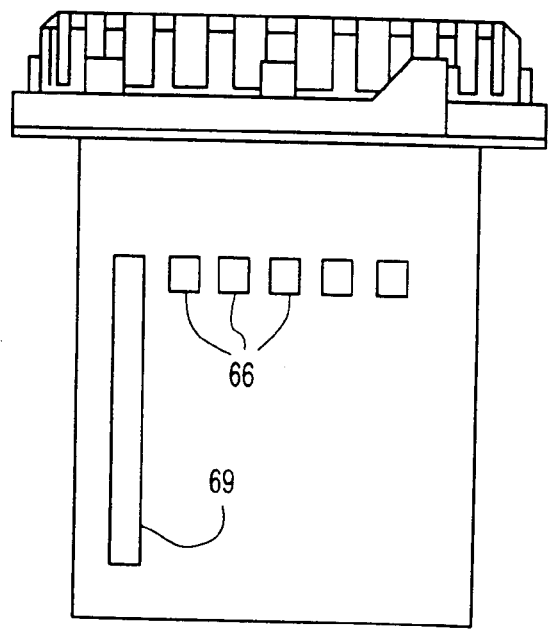
FIG. 8 is a side view of the specimen collecting apparatus according to the present invention illustrating structure for observing the results of the diagnostic testing.

After the fluid releasing device has been activated and the sample fluid has been introduced into the fluid flow path 32, the sample fluid advances along the test agent 95 preferably through capillary action and is tested, for example, for the presence of a predetermined analyte as described above. In one embodiment, the specimen container may include a transparent side wall portion to enable visual observation of test results, or to enable measurement by instrumentation. In a preferred embodiment, visual observation of test results may be made through windows 66 located preferably in the side of the container, as illustrated in FIG. 8. In this embodiment, the windows 66 may show a section of test agents 95 which illustrate a visual indication of the test results, such as, for example, a "+" for a positive test result and a blank for a negative test result. However, any number of different symbols may be used to identify the test results, as known to those skilled in the art. The windows 66 may also enable visual observation of a control test result, indicating the appropriate operation of the test, as known to those skilled in the art.

In another embodiment, the specimen container 15 may be made partially or completely constructed of a clear material, for example a suitable plastic, which permits visual observation or measurement by instrumentation of test agents 95 through the side of the container. In yet another embodiment, the specimen container may be provided with a window 69 which will permit visual confirmation that fluid has entered the isolation chamber 65, such as during a specimen collection phase, and visual confirmation that fluid has left the isolation chamber 65, such as during a testing phase. The window 69 preferably located in the side of the specimen container, or a portion thereof, and permits visual observation of the isolation chamber 65, as illustrated in FIGS. 3 and 8.

Figure 6A:
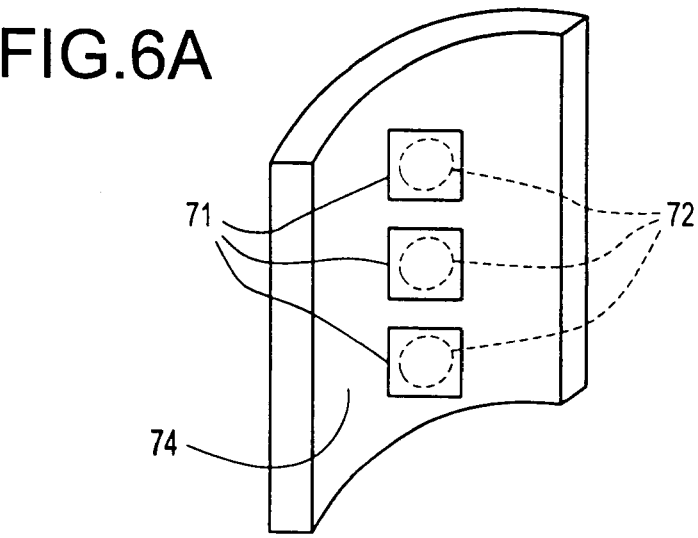
FIG. 6a illustrates the section of the isolation chamber of FIG. 6 with a porous membrane covering the apertures.
Figure 16:
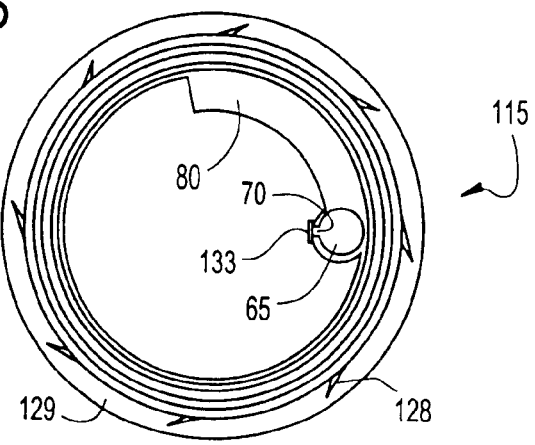
FIG. 16 illustrates a top view of the fluid testing and collecting apparatus illustrated in FIG. 14.

In another aspect of the present invention, the specimen container may be provided with a filter to filter the fluid specimen before it is tested. In one embodiment, the isolation chamber 65 may be provided with a porous membrane which can filter the fluid specimen before it enters the isolation chamber 65. For example, a porous membrane 133 may be provided over an opening 3 above open end 70 of isolation chamber 65, as illustrated in FIGS. 3 and 16. In one embodiment, porous membrane 133 may be provided preferably with an adhesive backing which will enable attachment to structure forming opening 3. In another embodiment, a porous membrane 71, preferably with an adhesive backing, may be provided over apertures 72, as illustrated in FIG. 6a.

While several embodiments of the invention have been described in some detail, it should be understood that the invention encompasses various modifications and alternative forms of those embodiments. For example, in an alternate embodiment, the isolation chamber 65 may be initially sealed from the collection chamber 40 instead of the test chamber 80. In this embodiment, the fluid releasing element 100 may break the seal on the isolation chamber 65 for a sufficient period of time to allow a specified amount of the fluid sample to flow into the isolation chamber 65. Once the specified amount of fluid has entered the isolation chamber 65, the fluid releasing element 100 must then re-seal the isolation chamber 65.

In still another embodiment, the isolation chamber 65 may be initially sealed from both the collecting chamber and the test chamber 80. In this embodiment, the fluid releasing element 100 breaks the seal between the isolation chamber 65 and the collecting chamber thus allowing the aliquot to flow into the isolation chamber 65. Subsequently, the fluid releasing element 100 breaks the seal between the isolation chamber 65 and the test chamber 80 while re-creating a seal between the collection chamber 40 and the isolation chamber 65 so that only the aliquot flows to the test chamber 80.

In yet another embodiment of the present invention, a fluid releasing element in the form of a plug 140 may be inserted into the isolation chamber 145 of a specimen container 150, as illustrated by FIGS. 9–11. In this embodiment, the isolation chamber 145 may be in fluid communication with collection chamber 143 through an open end 147 of the isolation chamber. The isolation chamber also may include a frangible bottom wall 149. Preferably, the plug 140 may be provided with a penetrating member 144 which, when pressure is applied from the lid 160, may penetrate or break the frangible bottom wall 149 enabling the fluid sample to flow to a fluid flow path 152, as illustrated in FIG. 11. At the same time that it breaks the frangible bottom wall 149, plug 140 seals the isolation chamber 145 from the collection chamber 143. To facilitate sealing, the plug 140 may include a stopper 142 at a first end, as illustrated in FIG. 9. Sealing may be initiated by applying pressure to the plug 140 to force the stopper 142 into engagement with the open end 147 of the isolation chamber 145 thereby creating a fluid tight seal. For example, as lid 160 is coupled to the container, the lid 160 may apply pressure on the plug 140, drive the element through the frangible bottom wall 149 of the isolation chamber 145, while plugging the open end 147 of the isolation chamber 145, as illustrated in FIG. 11.

In an alternative embodiment, the penetrating member 144 of plug 140 may be sized so that it forms a fluid tight seal at or near the bottom of the isolation chamber 145, while permitting fluid to enter the isolation chamber through the open end 147. By applying pressure to the upper portion of plug 140, the stopper 142 is forced into the open end 147 of the isolation chamber 145 forming a fluid tight seal. The penetrating member 144 concurrently may be forced through the bottom end of the isolation chamber 145 thereby opening communication with the fluid path 152. In this embodiment, frangible bottom wall 149 is not provided in isolation chamber 145, and a fluid tight seal is maintained at all time between the test chamber 155 and the collection chamber 145.

Figure 12:
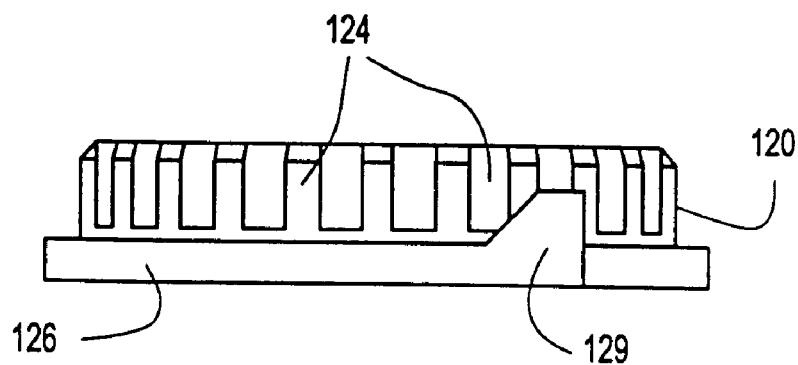
FIG. 12 illustrates a side view of the tamper evident lid in accordance with the present invention.
Figure 13:
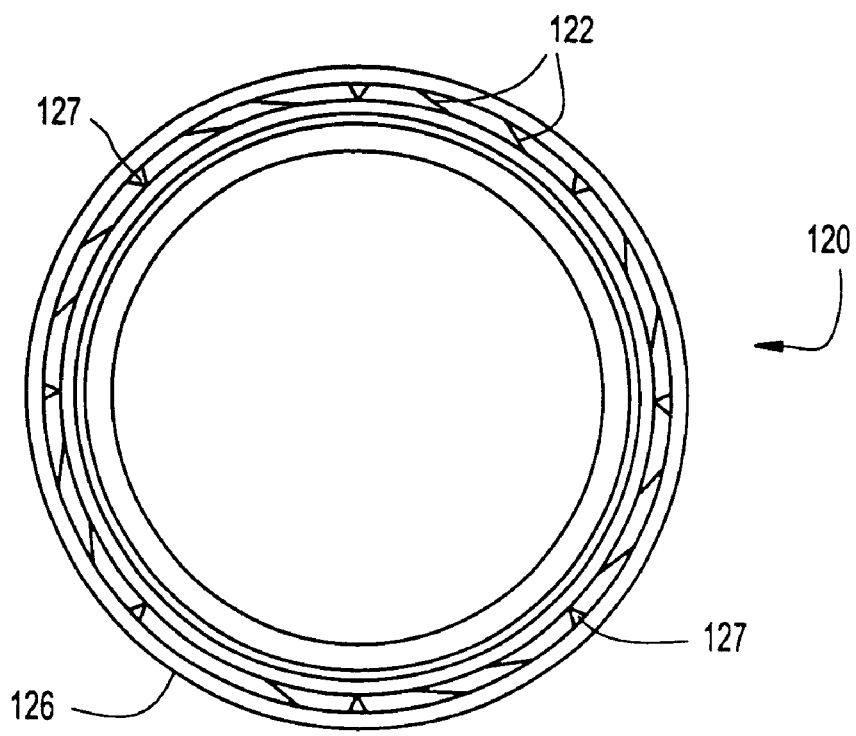
FIG. 13 illustrates a bottom view of the tamper evident lid shown in FIG. 12.

In still another embodiment of the present invention, the specimen container may include a tamper evident lid that provides an indication of whether or not the container has been opened which may indicate that the contents of the container have been compromised. As illustrated in FIG. 12, the tamper evident lid 120 may include a top portion having rib structures 124, which facilitate rotation of the lid around the specimen container, and may include a tamper strip 126. As illustrated in FIG. 13, tamper strip 126 may be attached to lid 120 by connection knobs 127 disposed around the inner periphery of strip 126. Teeth 122 preferably are disposed about the inner periphery of strip 126 and permit one-way rotation of the lid 120 around the specimen container. Teeth 122 form an acute angle with the strip 126 as illustrated in FIG. 13.

Figure 14:
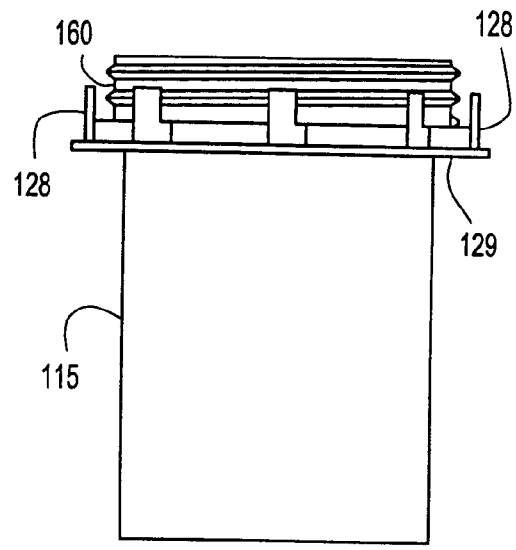
FIG. 14 illustrates a side view of the fluid testing and collecting apparatus to which the tamper evident lid is attached.
Figure 15:
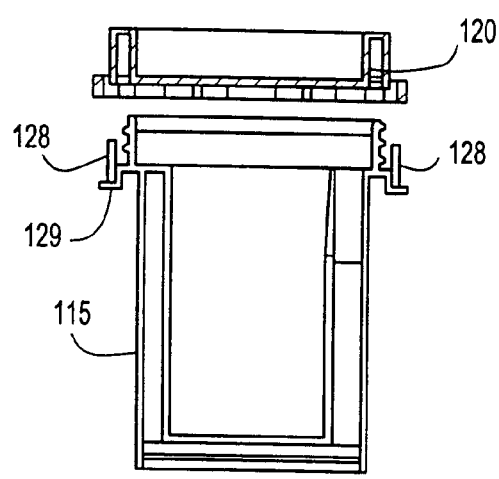
FIG. 15 illustrates a cross-sectional view of the fluid testing and collecting apparatus and the tamper evident lid in accordance with the present invention.

In one embodiment of the invention, the tamper evident lid 120 may be rotatable around a rim 160 of a specimen container 115, which is illustrated in FIGS. 14–16. The specimen container preferably may include a ledge 129 provided on the circumference of the specimen container and preferably may be located at or below the lower edge of rim 160. Ledge 129 also preferably may include barbs 128 extending upward therefrom which are mateable with teeth 122 of the tamper evident strip 126. The bards 128 and teeth 122 allow for easy rotation of the lid 120 around the rim 160 during closure. However, when the lid 120 is turned in an opposite direction, the barbs 128 mate with the teeth 122 on strip 126 thereby preventing further rotation of the lid 120. If sufficient force is applied to lid 120 in an attempt to continue opening the container, the connection knobs 127 will break causing the strip 126 to be completely or partially disconnected from the lid 120. Evidence that the strip 126 has been partially or completely disconnected from the lid 120 may reflect that the specimen container 115 has been tampered with and that the contents of the container have been compromised.

In a preferred embodiment, the tamper evident lid 120 may be rotatable to a first position forming a fluid tight seal over the specimen container, and then to a second position which activates the fluid releasing element 100. The first position may be characterized by rotation of the lid 120 to a region where the teeth 122 begin to engage the barbs 128. This first position is signified by a clicking sound of the teeth engaging the barbs. In a further aspect of a preferred embodiment, teeth 122 may first engage the barbs 128 after approximately 360 degrees of rotation. Of course, the lid 120 and specimen container 115 may be constructed such that the teeth 122 first engage the barbs 128 after a smaller or larger angle of rotation. In one embodiment, the lid 120 does not cause activation of the fluid releasing device 100 in the first position.

When it is desired to initiate the diagnostic testing of the fluid sample, the tamper evident lid 120 may be rotated from the first position to a second position which activates the fluid releasing device 100. In a preferred embodiment, the second position may be reached after approximately 360 degrees of rotation from the first position. Of course, the second position may be reached after a smaller or larger rotation from the first position.

In another aspect of a preferred embodiment, the tamper strip 126 may be removed at any time using any suitable structure for removal such as, for example, the tab 129, as illustrated in FIG. 12.

Figure 17:
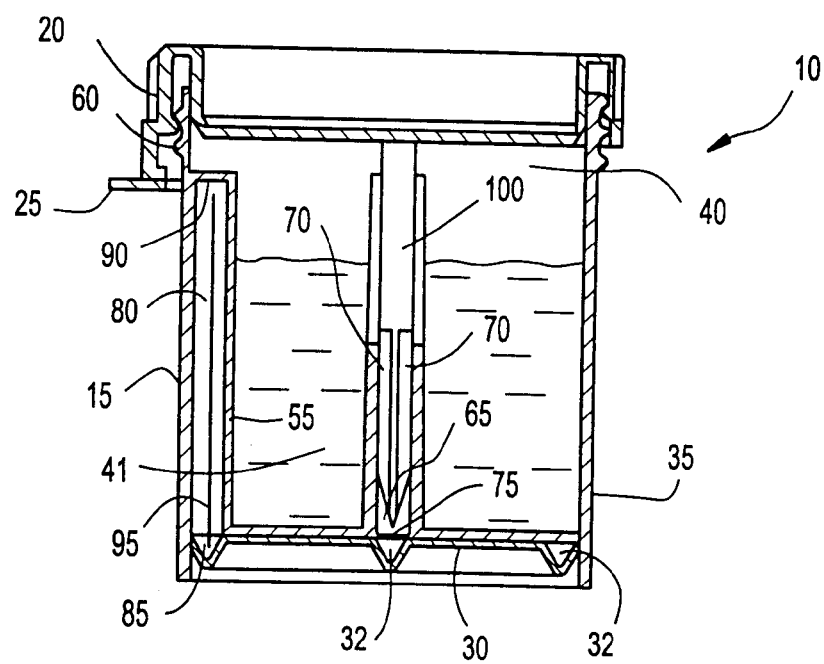
FIG. 17 illustrates a cross sectional view of the specimen collecting cup in accordance with yet another alternative embodiment of the present invention.

In yet another embodiment of the present invention, the specimen container 15 may be provided with an isolation chamber 65 which is located in the center of the collection chamber 40, as illustrated in FIG. 17. As described above in connection with FIGS. 1–3, the fluid enters the isolation chamber 65 through the open end 70 thereof. When the lid 20 is coupled with specimen container 15, the fluid releasing element 100 is driven through the frangible bottom wall 75 to direct the fluid specimen to the fluid flow path 32 and to the test chamber 80. In addition, the fluid releasing element 100 arrests fluid flow from the collection chamber 40 to the isolation chamber 65 in such a manner as to prevent establishment of a direct flow path between the collection chamber 40 and the test chamber 80, as described above.

In another embodiment, the fluid releasing device 100 may be mounted to and is rotatable with the lid 20, as illustrated in FIG. 17. In operation, the fluid specimen is placed in collection chamber 40 and enters isolation chamber 65 through the open end 70. The fluid releasing element 100 connected to lid 20 may be inserted into the isolation chamber 65. The lid 20 and isolation chamber 65 are rotatable together to close the lid 20 around the rim 60 of the specimen container 15. Lid 20 and fluid releasing element 100 preferably are rotatable to a first phase, as illustrated in FIG. 17 and described above in connection with FIG. 1, and to a second phase, as described above in connection with FIG. 2.

In this embodiment, the lid 20 and fluid releasing element 100 may be connected together by any suitable means. For example, the lid 20 and fluid releasing element 100 may be formed of a single, unitary structure. In an alternative embodiment, the fluid releasing device may be mounted to the lid by a suitable adhesive.

Figure 22:
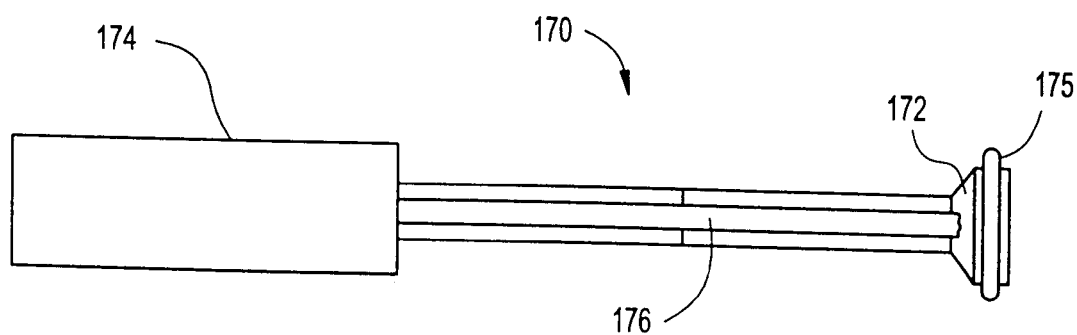
FIG. 22 illustrates a fluid releasing element in accordance with another embodiment of the present invention.

In still another embodiment of the present invention, a fluid releasing element 170 may be inserted into an isolation chamber 65 of a specimen container 15, as illustrated in FIGS. 18–22. As shown in FIG. 22, the fluid releasing element 170 has a solid portion 174 at one end and a plug 172 at the other end. Plug 172 is sized so that it forms a fluid tight seal at or near the bottom of the isolation chamber 65. Plug 172 may have a structure around a base thereof which facilitates the formation of the fluid tight seal. In a preferred embodiment, an o-ring 175 may be provided on plug 172, as illustrated in FIG. 22, to facilitate the formation of the fluid tight seal. Solid portion 174 is sized so that a fluid tight seal may be formed between the isolation chamber 65 and the collection chamber 40 through open end 70. Fluid releasing element 170 may also include a shaft 176 which connects the solid portion 174 with the plug 172. Shaft 176 is sized so as to permit, in combination with the diameter of isolation chamber, a predetermined amount of fluid in the isolation chamber.

Figure 18:
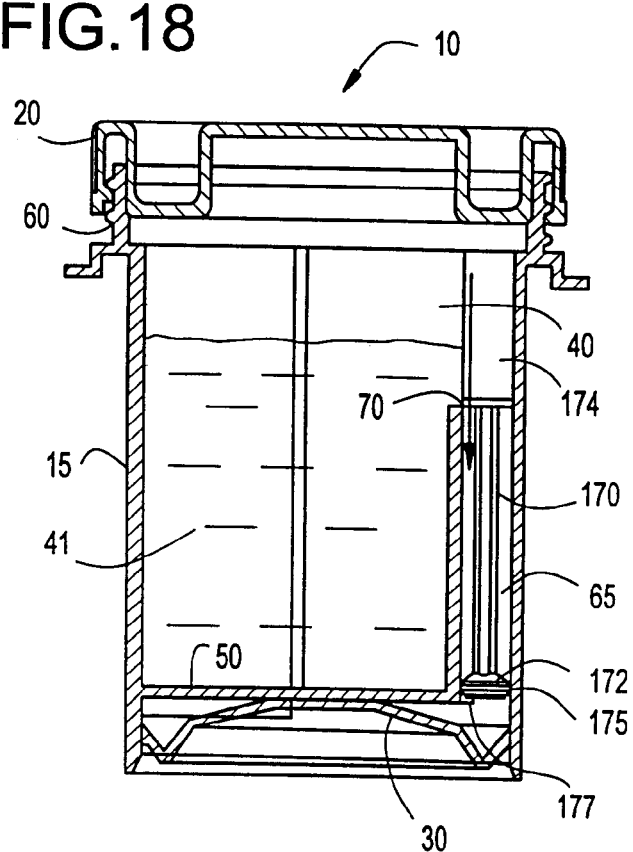
FIG. 18 illustrates a cross sectional view of the fluid collecting and testing apparatus according to another alternative embodiment of the present invention in a first phase of operation.
Figure 19:
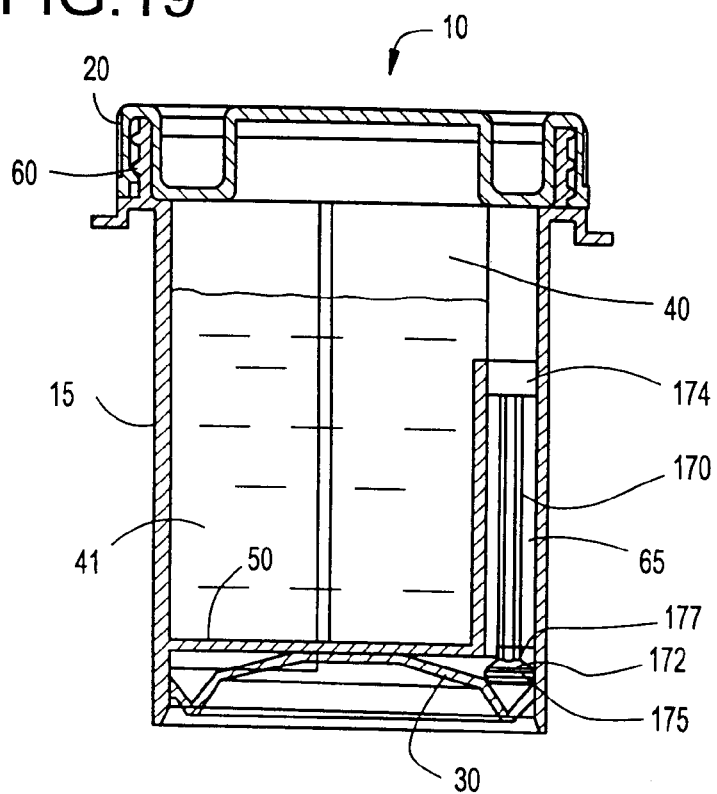
FIG. 19 illustrates a cross sectional view of the fluid collecting and testing apparatus according to the embodiment of FIG. 18 in a second phase of operation.
Figure 20:
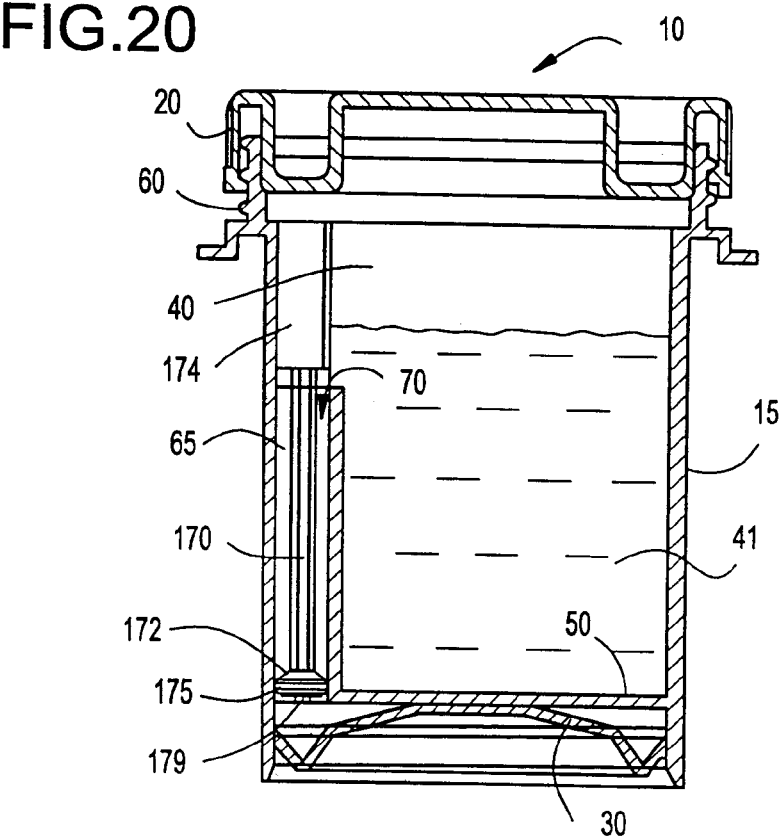
FIG. 20 depicts a cross sectional view of the fluid collecting and testing apparatus according to an another alternative embodiment of the present invention in a first phase of operation.
Figure 21:
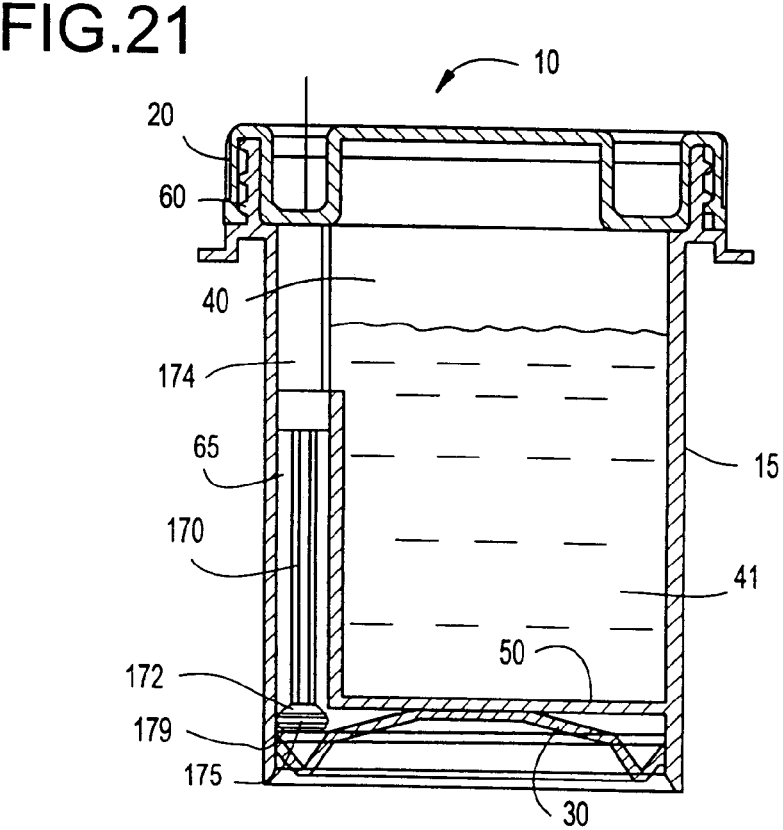
FIG. 21 illustrates a cross sectional view of the fluid collecting and testing apparatus according to the embodiment of FIG. 20 in a second phase of operation.

In this embodiment, the isolation chamber 65 does not include a frangible bottom wall, but instead has an open end, as illustrated in FIGS. 18–21. A fluid tight seal is maintained between the test chamber 80 and the collection chamber 40 by the plug 172 on the fluid releasing element 170. The plug 172 may provide a fluid tight seal at or near the bottom of the isolation chamber 65, while fluid is permitted to enter the isolation chamber 65 through the open end 70, as illustrated in FIGS. 18 and 20. By applying pressure to the upper portion of the fluid releasing element 170, the solid portion 174 is forced into the open end 70 of the isolation chamber forming a fluid tight seal between the collection chamber 40 and the isolation chamber 65. The plug 172 concurrently may be forced through the bottom end of the isolation chamber 65 thereby opening communication between the isolation chamber 65 and the fluid flow path 32, as illustrated in FIGS. 19 and 21. For example, as lid 20 is coupled to the container, the lid 20 may apply pressure on the fluid releasing element 170, driving the plug 172 through the bottom end of the isolation chamber, while plugging the open end 70 of the isolation chamber 65 with the solid portion 174. In this embodiment, as with the other embodiments, a fluid tight seal is maintained at all times between the test chamber 80 and the collection chamber 40.

In accordance with another embodiment of the present invention, a small section of a bottom portion of the isolation chamber 65 may be removed to enhance fluid flow from the isolation chamber 65 to the testing chamber 80. For example, as illustrated by FIGS. 18–19, a notch 177 may be removed from bottom of isolation chamber 65 which provides an increased area through which fluid may flow from the isolation chamber. In another embodiment, a nick 179 may be removed from the bottom of isolation chamber 65 which provides an increased area through which fluid may flow from the isolation chamber, as illustrated in FIGS. 20 and 21. In accordance with a preferred embodiment, notch 177 and nick 179 are both removed from bottom of isolation chamber 65 to enhance fluid flow from the isolation chamber to the testing chamber. As shown in FIGS. 18 and 20, the plug 172 maintains a fluid tight seal in the isolation chamber at or above the notch 177 and/or nick 179.

Also in accordance with a preferred embodiment, the notch 177 formed in the isolation chamber is larger than nick 179. Further, the notch 177 may be formed in the wall of the isolation chamber that is closest to the testing chamber, and nick 179 may be formed in the wall of the isolation chamber furthest from the testing chamber.

The various embodiments of the invention as described above refer to chambers. It is intended that the invention is not limited to a chamber, but may include any structure that functions as described above. For example, the collection chamber may be a region; or the isolation chamber may be a channel or conduit. Furthermore, it is intended that the invention is not to be limited by the number or relative sizes of chambers. For example, an embodiment of the invention may include a two-part isolation chamber, each part separated by a fluid tight seal or the like. In this embodiment of the invention, the first part of the isolation chamber comprises structures used to separate a portion of the fluid from the fluid in the collection chamber. The second part of the isolation chamber may include the test structures.

As noted above, the structure and function of the lid may include various structures, and closing the lid may include a number of stages of closure. It is intended that in some embodiments of the invention, the lid is merely a mechanism for providing a fluid-tight seal. In other embodiments of the invention, the lid may also be used to activate or establish fluid communication between the collection chamber and the isolation chamber. Alternatively, the lid may include a resilient portion that permits the operator to manually push the fluid releasing element through the frangible seal. In another alternative, the lid may include a piercing or slicing member on the inside underside of the lid that can open a membrane or the like that covers the top of the isolation chamber. manually push the fluid releasing element through the frangible seal. In another alternative, the lid may include a piercing or slicing member on the inside underside of the lid that can open a membrane or the like that covers the top of the isolation chamber.

As noted above, the preferred position of the test chamber is on a side wall of testing apparatus 10. It is intended that the invention is not to be limited by the location or size of the test chamber, except that the test chamber is not to be in direct fluid communication with the collection chamber. For example, the test chamber or test structures may be a discrete portion of the isolation chamber, may be in a bottom region of the testing apparatus, or may be positioned in the lid.

In an embodiment of the invention in which the test structure is located in the lid, the lid preferably closes the testing apparatus in at least two stages. In a first stage, the lid seals the collection chamber. This first stage may further include opening fluid communication between the collection chamber and the isolation chamber. In a second stage, such as further closing a rotatable lid, the lid includes structures that open or establish communication between the isolation chamber and the test area in the lid. For example, the isolation chamber may be a channel (without a plunger or spike) open at the bottom or having sealable apertures, and having a frangible covering on a top portion of the channel. When the lid is moved to its second position, a portion of the lid breaks the seal, thereby establishing fluid communication between the isolation channel and the test area.

In another embodiment of the invention, a method or apparatus according to the invention includes test structures for performing multiple tests for a single analyte, wherein each tests for a different quantity, threshold amount, or cut-off amount of the analyte. For example, such a device or method may include at least two test strips, preferably about five or six test strips, with the first test strip providing an indication of the presence of 10 mg of analyte in the sample, the second test strip indicating 20 mg, the third test strip indicating 30 mg, and so on as desired. Such an embodiment of the invention may be particularly suited for determining the presence and amount of cholesterol or alcohol in the sample. In these and other examples, it may be desirable for the first two or three test strips to provide an indication of the amount of analyte in the sample that is below a legal or desirable amount. Another test strip may indicate the exact legal or desirable amount, and other test strips may indicate progressively higher amounts over the legal or desirable amount. In these embodiments of the invention, the method and apparatus provides quantitative or semi-quantitative test results.

In yet another embodiment of the invention, a method or apparatus according to the invention includes multiple devices that include one or more test structures for performing multiple tests for multiple analytes. For example, a first device or method may include at least one test for a class of analytes, e.g. a series of allergens. If the first device provides a positive indication for a particular class, a second device or method may include divisions or species within that class. For example, if the first device is positive for pollen, a second device may test various types of pollen. Thus, in accordance with an embodiment of the invention, multiple devices may be used in conjunction with each other to specifically diagnose or detect a specific analyte or a specific type of analyte.

In addition to the preceding, the invention covers all other modifications, equivalents and alternatives falling within the spirit and scope of the claims.

We claim:

1. A fluid specimen collecting and testing apparatus comprising:
   a specimen container;
   a first chamber disposed within the specimen container for collecting a fluid specimen;
   a second chamber in fluid communication with said first chamber;
   a third chamber sealed from the first and second chambers, said third chamber including a fluid testing device;
   a fluid releasing element moveably engagably within said second chamber to release the fluid specimen from said second chamber and establish a fluid flow path between the second and third chambers and to seal the second chamber from said first chamber,
   wherein said fluid flow path between the second and third chambers has a substantially "v-shaped" cross section.

2. The fluid specimen collecting and testing apparatus according to claim 1 wherein said second chamber comprises a frangible bottom wall which when pierced by said fluid releasing element establishes the fluid flow path between the second and third chambers.

3. The fluid specimen collecting and testing apparatus according to claim 2 wherein said fluid releasing element comprises a plug on one end and a stopper on an opposite end.

4. The fluid specimen collecting and testing apparatus according to claim 3 wherein said plug of said fluid releasing element penetrates said frangible bottom wall.

5. The fluid specimen collecting and testing apparatus according to claim 3 wherein said stopper of said fluid releasing element seals said second chamber from said first chamber.

6. The fluid specimen collecting and testing apparatus according to claim 1 wherein said fluid releasing element comprises a spike on one end and a solid portion on an opposite end.

7. The fluid specimen collecting and testing apparatus according to claim 6 wherein said solid portion of said fluid releasing element seals said second chamber from said first chamber.

8. The fluid specimen collecting and testing apparatus according to claim 6 wherein said fluid releasing element further comprises grooves for enabling said fluid specimen to flow from said first chamber into said second chamber.

9. The fluid specimen collecting and testing apparatus according to claim 8 wherein said grooves of said fluid releasing element permit an aliquot of fluid specimen of a predetermined volume to flow from said first chamber into said second chamber.

10. A fluid specimen collecting and testing apparatus comprising:
    a specimen container;
    a first chamber disposed within the specimen container for collecting a fluid specimen;
    a second chamber in fluid communication with said first chamber;
    a third chamber sealed from the first and second chambers, said third chamber including a fluid testing device;
    a fluid releasing element moveably engagably within said second chamber to release the fluid specimen from said second chamber and establish a fluid flow path between the second and third chambers and to seal the second chamber from said first chamber; and further comprising a tamper evident lid having a plurality of teeth which permit one-way rotation of said tamper evident lid.

11. The fluid specimen collecting and testing apparatus according to claim 10 wherein said teeth engage barbs on said fluid specimen and collecting apparatus which prevents rotation of said lid in a direction opposite to said one-way rotation.

12. The fluid specimen collecting and testing apparatus according to claim 11 wherein said tamper evident lid further comprises a removable tamper strip connected to around the circumference of said lid by connection knobs.

13. The fluid specimen collecting and testing apparatus according to claim 12 wherein said teeth are connected to said removable tamper strip.

14. The fluid specimen collecting and testing apparatus according to claim 12 wherein said tamper strip is removable from said lid when said lid is rotated in a direction opposite to said one-way rotation after said teeth become engaged with said barbs.

15. A fluid specimen collecting and testing apparatus comprising:
   a specimen container;
   first chamber disposed within the specimen container for collecting a fluid specimen;
   a second chamber in fluid communication with said first chamber;
   a third chamber sealed from the first and second chambers, said third chamber including a fluid testing device;
   a fluid releasing element moveably engagably within said second chamber to release the fluid specimen from said second chamber and establish a fluid flow path between the second and third chambers and to seal the second chamber from said first chamber, wherein said second chamber comprises an open bottom end, wherein said fluid releasing element comprises a plug on one end and a solid portion on an opposite end, and further comprising a tamper evident lid having a plurality of teeth which permit one-way rotation of said tamper evident lid.

16. The fluid specimen collecting and testing apparatus according to claim 15 wherein said plug is able to provide a fluid tight seal between said second chamber and said third chamber.

17. The fluid specimen collecting and testing apparatus according to claim 15 wherein said solid portion of said fluid releasing element is able to seal said second chamber from said first chamber.

18. The fluid specimen collecting and testing apparatus according to claim 15 wherein said fluid releasing element is engageable within said second chamber such that there is fluid communication between said first chamber and said second chamber while said plug provides a fluid tight seal between said second chamber and said third chamber.

19. The fluid specimen collecting and testing apparatus according to claim 15 wherein said fluid releasing element is engageable within said second chamber such that said solid portion provides a fluid tight seal between said first chamber and said second chamber while said plug penetrates through said open end of said second chamber thereby enabling fluid communication between said second chamber and said third chamber.

20. A fluid specimen collection and testing apparatus comprising:

a specimen container including a bottom wall and a retaining wall extending from the bottom wall, the bottom wall including a fluid flow path;

a tamper evident lid having a plurality of teeth which permit one-way rotation of said lid coupled to said specimen container, a collection chamber disposed within said specimen container for collecting a fluid specimen, an isolation chamber in fluid communication with said collection chamber, said isolation chamber including a frangible bottom wall and a retaining wall, the bottom wall being disposed adjacent the fluid flow path;

a test chamber sealed from said collection and isolation chambers, said test chamber having an open end disposed adjacent the fluid flow path, and said test chamber including a fluid testing device; and, a fluid releasing element coupled with said isolation chamber to, upon engagement with said lid, release the fluid specimen from said isolation chamber and to permit the fluid specimen to flow along the fluid flow path to the test chamber, and to seal said isolation chamber from said collection chamber.

21. A fluid specimen collecting and testing apparatus comprising:
   a collection chamber for collecting a fluid specimen, said collection container including a bottom wall and a retaining wall extending from the bottom wall;
   an isolation chamber in fluid communication with said collection chamber, said isolation chamber including a retaining wall;
   a test chamber which is sealable from said collection and isolation Chambers, said test chamber including a fluid testing device; and,
   a fluid releasing element moveably engaged within said isolation chamber such that there is fluid communication between said collection chamber and said isolation chamber while said fluid releasing element provides a fluid tight seal between said isolation chamber and said test chamber, and such that said fluid specimen releasing element provides a fluid tight seal between said collection chamber and said isolation chamber while said fluid releasing element exposes an opening of said isolation chamber thereby enabling communication between said isolation chamber and said test chamber, further comprising a tamper evident lid engageable with said collection chamber, wherein said tamper evident lid has a plurality of teeth which permit one way rotation of said tamper evident lid.

22. The fluid specimen collecting and testing apparatus according to claim 21 wherein said teeth engage barbs on said fluid specimen and collecting apparatus which prevents rotation of said lid in a direction opposite to said one-way rotation.

23. A method for collecting and testing a fluid specimen, said method comprising:
   collecting a fluid specimen in first chamber of a specimen container, the specimen container having;
   a second chamber in fluid communication with said first chamber;
   a third chamber sealed from the first and second chambers, said third chamber including a fluid testing device;
   a fluid releasing element moveably engagably within said second chamber to release the fluid specimen from said second chamber and establish a fluid flow path between the second and third chambers and to seal the second chamber from said first chamber, wherein said fluid flow path) between the second and third chambers has a substantially "v-shaped" cross section;

isolating a portion of the fluid specimen in said second chamber;

blocking fluid flow from the first chamber to the second chamber;

sealing the third chamber from the first chamber;

directing the isolated portion to the third chamber; and, testing the isolated portion using the fluid testing device.

24. A method for collecting and testing a fluid specimen, said method comprising:

collecting a fluid specimen in first chamber of a specimen container, the specimen container having:

a tamper evident lid engageable with said first chamber, wherein said tamper evident lid has a plurality of teeth which permit one way rotation of said tamper evident lid;

a second chamber in fluid communication with said first chamber;

a third chamber sealed from the first and second chambers, said third chamber including a fluid testing device; and, a fluid releasing element moveably engagably within said second chamber to release the fluid specimen from said second chamber and establish a fluid flow path between the second and third chambers and to seal the second chamber from said first chamber;

isolating a portion of the fluid specimen in said second chamber;

blocking fluid flow from the first chamber to the second chamber;

sealing the third chamber from the first chamber;

directing the isolated portion of the fluid specimen to the third chamber; and, testing the isolated portion using the fluid testing device.

* * * * *